United States Patent [19]

Dodt et al.

[11] Patent Number: 4,767,742

[45] Date of Patent: Aug. 30, 1988

[54] HIRUDIN-PA AND ITS DERIVATIVES, PROCESS FOR MANUFACTURING THESE AND THE USE OF THESE SUBSTANCES

[75] Inventors: Johannes Dodt; Ursula Seemuller, both of Munich; Hans Fritz, Hohenbrunn; Ernst Fink, Westerstede-Geissbelhorst, all of Fed. Rep. of Germany

[73] Assignee: Plantorgan-Werk Heinrich G. F. Christensen, KG, Bad Zwischenahn, Fed. Rep. of Germany

[21] Appl. No.: 897,610

[22] PCT Filed: Dec. 12, 1985

[86] PCT No.: PCT/EP85/00701

§ 371 Date: Aug. 6, 1986

§ 102(e) Date: Aug. 6, 1986

[87] PCT Pub. No.: WO86/03493

PCT Pub. Date: Jun. 19, 1986

[30] Foreign Application Priority Data

Dec. 13, 1984 [DE] Fed. Rep. of Germany ....... 3445532

[51] Int. Cl.$^4$ ...................... A61K 37/43; C07K 7/10
[52] U.S. Cl. ....................................... 514/12; 530/324
[58] Field of Search ........................... 530/324; 514/12

[56] References Cited

FOREIGN PATENT DOCUMENTS 0142860  5/1985  European Pat. Off. .

OTHER PUBLICATIONS

Dodt et al., Chemical Abstracts, vol. 105, No. 167762y (1986).
Petersen et al., Chemical Abstracts vol. 85, No. 105932p (1976).
Chang, Chemical Abstracts vol. 100, No. 152937g (1984).
Dodt et al., Chemical Abstracts vol. 100, No. 152937g (1984).

*Primary Examiner*—John Kight
*Assistant Examiner*—Christina Chan
*Attorney, Agent, or Firm*—Birch, Stewart, Kolasch & Birch

[57] ABSTRACT

The present invention relates to a new content substance found in leeches (*Hirudo medicinalis*), the derivatives of this abbreviated at the N-terminus and the C-terminus, and the desulfated derivatives therefrom as well as a process for the production of these compounds, and their use. These compounds possess thrombin-inhibiting properties and can be used to inhibit clotting in human and animals, for blood conservation, or as reagents for the analytical determination of thrombin.

11 Claims, 3 Drawing Sheets

E D A Ÿ D E          Ÿ = Tyrosin-O-Sulfate
 ─ ─ ─ ─→
 ←─←─←─←─←─
```

HIRUDIN-PA AND ITS DERIVATIVES, PROCESS FOR MANUFACTURING THESE AND THE USE OF THESE SUBSTANCES

FIELD OF THE INVENTION

The present invention relates to hirudin-PA and its derivatives, a process for manufacturing these substances, pharmaceuticals that contain these substances, and the use of these substances.

BACKGROUND OF THE INVENTION

Several substances have already been extracted from medicinal leeches (hirudo medicinalis) such as polypeptides that act as proteinase inhibitors and which have, in part, an antithrombin action. In the literature that deals with these substances, a distinction is drawn between the so-called eglines and hirudins. Two eglines are described in DE-PS No. 28 08 396. The extraction of crude hirudin is described in *Die Pharmazie*, Number 36, 1981, pages 653-660 and in *Methods in Enzymology*, Volume 45, 1976, pages 669-678. The complete amino acid sequence is known from FEBS 1104 (*Federation of European Biochemical Societies*, Volume 165, 1984, pages 180-184).

SUMMARY OF THE INVENTION

Most surprisingly, it has now been found that crude hirudin contains another component that is pharmacologically active.

For this reason, the present invention undertakes the examination of leech extracts for new pharmacologically effective substances, in particular the hirudin components of leech extracts more precisely for new substances.

According to the present invention, the solution to this task lies in the preparation of new hirudin components, designated hirudin-PA, their decomposition products, and the desulfated derivatives therefrom.

The present invention relates to hirudin-PA of formula I:

```
            10                  20
   I T Y T D C T E S G Q N L C L C E G S N
            30                  40
   V C G K G N K C I L G S Q G K D N Q C V
            50                  60
   T G E G T P K P Q S H N Q G D F E P I P
                       *            *
   E D A Y D E,            Y—Tyrosin—O—Sulfate
``` the derivatives of these substances, shortened at the N-terminus by up to 2 amino acids and at the C-terminus by up to 17 amino acids as well as the desulfated derivatives, in which, in the above formula I: (i) the sulfate ester group at the phenolic hyroxyl of the tyrosin group in position 64 is missing, or (ii) the sulfate ester group described at (i) and the latter or the two last amino acids D, E (in position 66 or 66+65) are missing, and the pharmaceutically useful salts thereof.

A preferred embodiment are hirudin-PA and its derivatives of formula I, the amino acid chain at the N-terminus being shortened by the sequence I or IT.

A further preferred embodiment are hirudin-PA and its derivatives wherein the amino acid chain at the C-terminus is shortened by the sequence:

Q S H N Q G D F E P I P E D A Y* D E,
E P I P E D A Y* D E.
P I P E D A Y* D E.
E D A Y* D E or
A Y* D E

Especially preferred is hirudin-PA of the formula I

```
            10                  20
   I T Y T D C T E S G Q N L C L C E G S N
            30                  40
   V C G K G N K C I L G S Q G K D N Q C V
            50                  60
   T G E G T P K P Q S H N Q G D F E P I P
                       *            *
   E D A Y D E            Y—Tyrosin—O—Sulfate
``` and its sulfated derivatives as defined above.

In the preceding formulae the quoted letters symbolize the proteinogenic amino acids that are peptidically linked, these letters corresponding to the IUPAC nomenclature. The salts of these proteins are also the object of the present invention.

The hirudin-PA according to the present invention consists of a total of 66 amino acids; its molecular weight is 7087; its specific antithrombin activity is 680-720 IU/mg and the complex with thrombin has the dissociations constant $K_i = 4 \times 10^{-11} M$.

BRIEF DESCRIPTION OF THE DRAWINGS

FIG. 4 shows the complete sequence for hirudin-PA.

DETAILED DESCRIPTION OF THE INVENTION

Figure 1:
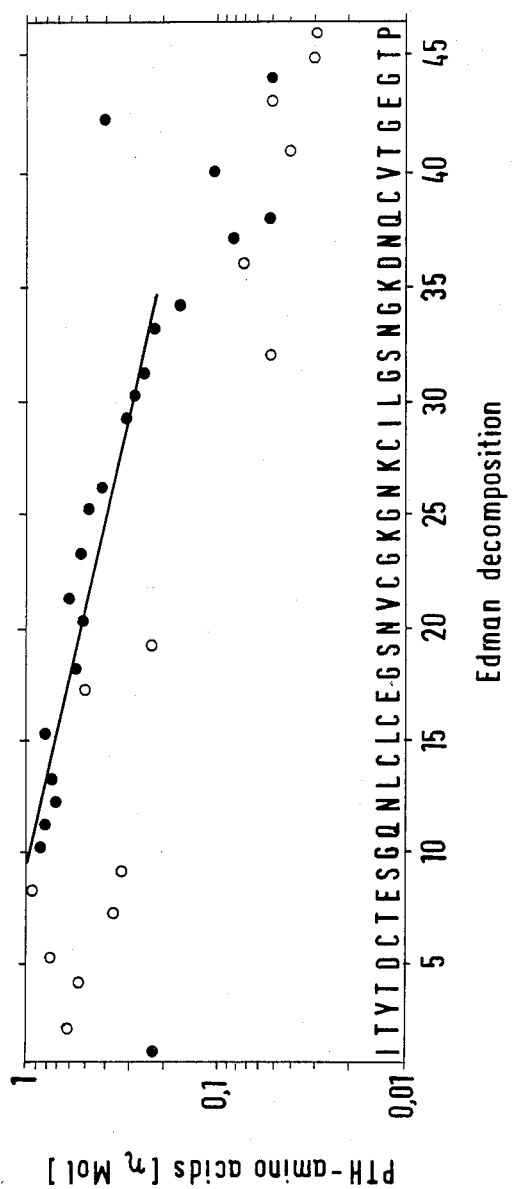
FIG. 1 is a graph showing the yields of PTH amino acids of the oxidized hirudin-PA.

Hirudine-PA and its derivatives are structurally very similar to the already known hirudin. However, at several important places on the protein chain, particularly at the beginning and at the end, the products according to the present invention differ in a characteristic manner from the sequence of the known hirudin. This results in further differences that are of great practical significance. The tertiary structure of these polypeptides is stabilized by three disulfide bridges. In hirudin-PA the strongly acid sulfate monoester group on the phenolic hydroxyl of the tyrosin group in position 64 is conspicuous; this can be represented by the following partial-structure formula:

$$\text{HO—SO}_2\text{—O—}\underset{\underset{\text{C=O}}{|}}{\overset{\overset{\text{NH}}{|}}{\text{C}_6\text{H}_4\text{—CH}_2\text{—CH}}} \quad [\text{Tyr}(\text{SO}_3\text{H})^{64}]$$

This grouping is also present in the known hirudin, although in this it is in position 63.

From the biological standpoint, hirudin with a $K_i$ value of approximately $3 \times 10^{-11} M$ belongs amongst the most effective thrombin inhibitors; it acts completely specifically against thrombin and inhibits no other proteinases of the blood clotting cascade. Unlike heparin, the hirudins according to the present invention exert their inhibiting influence on thrombin directly. Of their pharmacological effects, the inhibition of blood coagulation is important. The substances are thus particularly well suited for the prophylaxis of thromboses. No undesirable side-effects have been noted up to the present. During intravenous administration to dogs and human subjects there was no effect on heart rate, respiration, blood pressure, thrombocyte count, fibrinogens and haemoglobin. In comparative tests the compounds according to the present invention were superior to heparin.

In order to produce the hirudins according to the present invention one proceeds best from the known leech extracts. As has been discussed above, the production of extracts of this kind is described, for example, in *Die Pharmazie,* Number 36, 1981, pages 653–660 or in *Methods in Enzymology,* Volume 45, 1976, pages 669–678.

One proceeds in that leeches (*hirudo medicinalis*) or the head ends of leeches are reduced, homogenized, the tissue paste extracted with aqueous acetone or salt- or buffer-solution, a significant proportion of the impurities of the extract precipitated with ethanol during fractionation, the solution is reduced in a vacuum, the reduced solution is subjected to fractionating acetone precipitation, the precipitate obtained at higher acetone concentrations is reduced, this then being extracted, and the extract lyophilized. Proceeding from this lyophilisate that is familiar in and of itself, the process according to the present invention is characterized in that: (A) the lyophilisate that is obtained is chromatographed on a Sephadex column that has been equilibrated with a buffer of pH 7.8; (B) the fractions with antithrombin activity are lyophilised, the lyophilisate is desalinated, and lyophilised once again; (C) an anion exchange chromatography is carried out on DEAC cellulose with the lyophilisate, equilibration being carried out with a buffer of pH 6.5 and elutration being carried out with a buffer of pH 6.0; (D) the fractions that are antithrombin active are lyophilised, desalinated, and lyophilised; (E) the lyophilisate is placed in a DEAE-Sephadex column that has been equilibrated with a buffer of pH 6.0, elutriated with a buffer solution with a linear pH gradient that is formed from a buffer of pH 5.0 and a buffer of pH 3.7; (F) the fractions that are antithrombin active are elutriated at approximately pH 4.6 to 4.7 are lyophilised, desalinated, and again lyophilised; (G) finally, the lyophilisate is chromatographised on an HPLC column that is filled with a reversed phase sequestering agent of type $C_{18}$, with 0.1% trifluoracetic acid in water serving as elutriant (A) and 0.1% trifluoracetic acid in acetonitrile with 40% (A) (v/v) serving as elutriant (B)), with isocratic conditions ((63% (A)+37% (B)) predominating, when one obtains four thrombin-suppressing fractions, with the first of these containing the desired hirudin-PA; (H) to produce the desulfated forms of the hirudin-PA the sulfate monoester group on the phenolic hyroxyl of the tyrosin group in position 64, and if desired the amino acids D, E standing at the ends in positions 66, 65 are split off hydrolitically, either singly or together; (I) in order to produce the reduction decomposition products of the hirudin-PA this is incubated with a peptidase, the products separated through RP-HPLC, and the individual products isolated and lyophilised.

It is preferred that the chromatography in stage A be carried out on Sephadex G75, with an aqueous solution that contains 50 mM triethanolamin and 300 mM or 400 mM NaCl is used as a buffer of pH 7.8. In addition 0.02% $NaN_3$ can be added to this and to the buffer solutions described below.

It is preferred that the anion exchange chromatography be carried out on Whatman DE52 or DE53, with an ammonium acetate buffer (30 mM $NH_4Ac$ and optionally 0.02% $NaN_3$) used as an equilibrating buffer and a sodium acetate buffer composed of 0.2M NaAc and 0.19M NaCl used as an elutriation buffer with pH 6.0. It is also possible to use a salt gradient as an elutriation buffer, when one works first with 0.03M ammonium acetate, 0.19 m NaCl, pH 6.5, and finally with 0.03M ammonium acetate, 0.3M NaCl, ph 6.5.

It is preferred that a sodium acetate buffer of the above composition be used as a buffer of pH 6.0 during the Sephadex DEAE-A25 chromatography. The same buffer, on the one side at pH 5.0 and on the other at pH 3.7, is used to produce the pH gradient. The fractions that are elutriated at approximately pH 4.6 to 4.7 are antithrombin active and are designated hirudin pool 1. Fractions that are elutriated at approximately pH 4.4 are isolated as hirudin pool 2. The pool 1 that contains the antithrombin activity is then lyophilised, desalinated, and lyophilised again.

The desalination operations are as a rule carried out with Sephadex G25, with water serving as the wash agent. For the HPCL separation one can use, for example, a Type LC-18-DB Supelco column 5μ or a Type 100 CH-18/2 Lichrospher column, 5μ4.6×250 ml, by Merck.

Using a column of this kind, one works at a flow of 1 ml/min, at a temperature of 25° C., and detects at 214 and 254 nm.

During this HPLC separation of the hirudin pool 1 one obtains for thrombin-inhibiting fractions. The largest portion is identical with the hirudin known from the literature. Another small fraction differs from the known hirudin only by the exchange of an amino acid. The hirudin-PA according to the present invention is contained in the first and second strongest fraction. It is a completely new inhibitor type with N-terminal Ile and is described and sequenced as follows:

The protein of the above-described hirudin-PA fraction was immobilised in a solid phase and in this state subjected to the so-called Edman decomposition process. The standard technique of automatic solid phase sequencing employed in this instance is described, for example, in two survey articles by W. Machleidt *Modern Methods in Protein Chemistry—Revue Articles,* published in 1983 by Walter de Gruyter & Co., Berlin, New York, and by Richard A. Larsen and W. Machleidt in *Methods of Biochemical Analysis,* Volume 26, pages 201 to 284, 1980. The peptide that is to be sequenced is bonded covalently to the insoluble carrier, the solid phase, through functional groups of the amino acid side chains. In the solid phase it passes through the cyclic reactions of the Edman decomposition that lead to the separation of the specific N-terminal amino acids. The bonding of the peptide to the solid phase must be stable under the conditions of the Edman decomposition but must not, however, hinder the decomposition up to the C-terminus.

During this procedure, the phenylthiourea derivative of the cysteinic acid is particularly well-suited for the positive identification of the position of the cystine group. For this reason, sequence runs with native and oxidized hirudin-PA are carried out to clarify the N-terminal sequence. 25 nMol protein is used per run, half being immobilised though amino groups on diisothiocyanate glass (DTIC glass), and half through carbodiimide coupling of the carboxyl group on aminopropyl glass (APG). These two immobilizing techniques are described, for example, on pages 270 and 273 of the above references in W. Machleidt *Modern Methods in Protein Chemistry*, 1983. Since lysin groups couple at a high yield to DITC glass through their α-amino groups, mixed coupling entails the advantage that both the N-terminal amino acids and the position of the lysin radical can be determined in one sequence run.

It was first possible to clarify the sequence of the hirudin-PA up to position 46 (FIG. 1). The positions of the cystein groups and the lysin groups were established positively, although their phenylthiourea (PTH) derivatives were not quantified. Open circles symbolise the PTH derivatives of Asp, Glu, Ser, Thr and Pro. They represent those amino acids, of which the yields of PTH derivatives was lower. The repetitive yields of the sequence run of oxidized hirudin-PA (FIG. 1) was calculated as 94% for steps 10 to 34. At position 35, the lys 35 anchor point, the yield of PTH amino acids drops abruptly. These data indicate that still only a little material was bound through the last amino groups - anchor point 47, and at the same time the yields for the carboxyl groups coupling were low.

FIG. 1. Yields of PTH amino acids of the oxidized hirudin- PA.

The solid circles in positions 10 to 34 are used to calculate the regression lines. A repetitive yield of 94% resulted from the slope. The open circles were used for Asp, Glu, Pro, Thr, and Ser, which are either partially fixed to the carrier through side chains (Asp, Glu) or incompletely separated (Pro), or partially destroyed during the decomposition (Thr, Ser). Lysin was identified positively, but not quantified, however. Tryptic decomposition of oxidized hirudin-PA.

19 protein peaks were obtained during the separation of a tryptic separation batch by means of RP-HPLC. Description of the peptides was carried out by amino acid analysis and N-terminal determination with a one-step Handedman decomposition (DABITC/PITC double-coupling method) (Chang, Brauer, Wittmann-Liebold, 1978, *FEBS-Lett.*, Number 93, pages 205 to 214.). The TR 3 peptide was identified as tripeptide G-N-K that was associated with the known positions 25-27. The TR 16 peptide contained the C-terminal peptide with the former overlapping sequence information, beginning with 36 (Asp). After coupling to APG this was subjected to solid-phase Edman decomposition. The yield of these PTH derivatives was once again significantly lower, this being caused by the fixation of Asp and Glu. What has been said above also applies to the other derivatives. The yield of the second Edman step (Asn) was set at 100% and the other yields related to this figure. The slope of the regression lines for the solid circles revealed a repetitive yield of 93.3% (FIG. 2).

Comparison of the amino acid analysis and the amino acid composition after sequencing revealed a discrepancy of one amino acid:one Glx too established within the sequence. This amino acid had to the C-terminus, otherwise no indication of an additional Glx have been noted. A C-terminus sequencing with carboxypeptidase Y should be completed so as to clarify the C-terminus sequence and answer the question as to whether the tyrosin group is a tyrosin-O-sulfate groups as in the hirudin.

Figure 2:
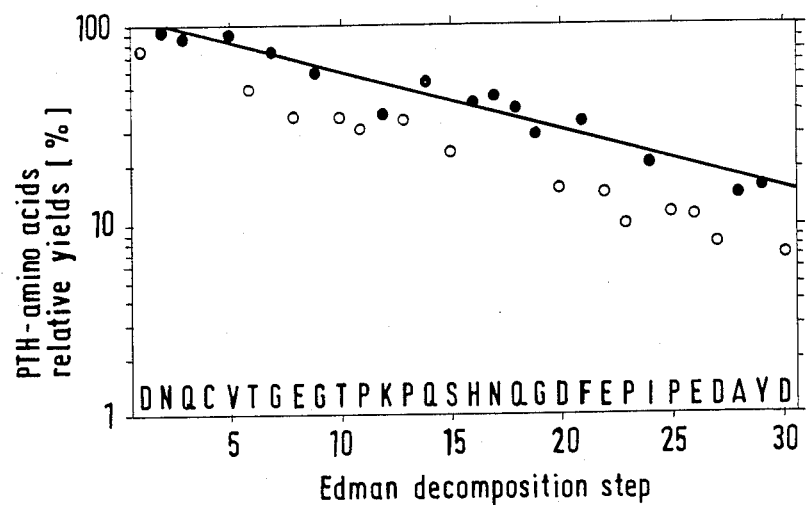
FIG. 2 is a graph showing the yields of PTH amino acids of tryptic peptide TR 16.

FIG. 2: Yields of PTH amino acids of tryptic peptide TR 16.

The yield from the second decomposition step according to Edman has been set at 100% and the remaining yields related to this. The solid circles were used to calculate the regression lines, and a repetitive yield of 93.3% was obtained from their slope. Open circles were used for Asp, Glu, Pro, Thr, and Ser amino acids (See FIG. 1). C-terminal sequencing of hirudin-PA with carboxy-peptidase Y (CPY).

Figure 3:
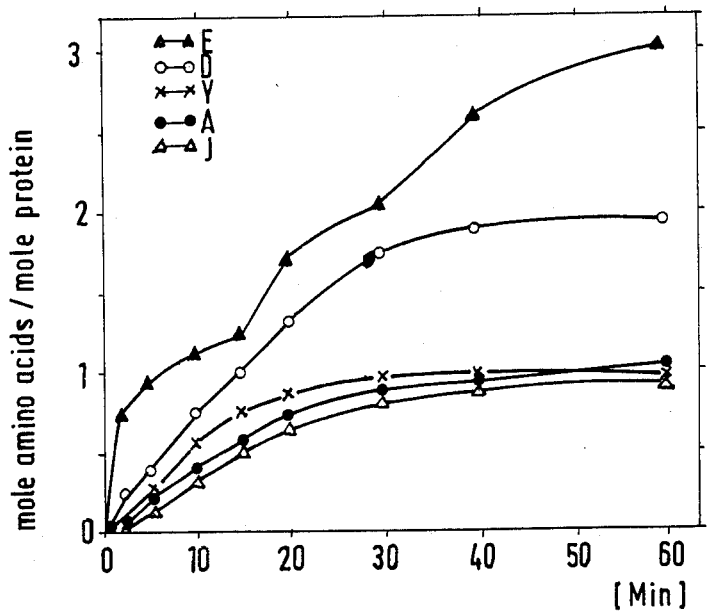
FIG. 3 is a time diagram for the CPY catalyzed liberation of the amino acids of the C-terminus of hirudin-PA.

The C-terminal sequencing of hirudin-PA is carried out from native hirudin-PA, the TR 16 peptide, and the TR 16 peptide that had been incubated previously for 30 minutes at 60° C. with 50% TFA. Initially, rapid separation of glutamin acid was observed prior to liberation of aspartic acid and additional amino acids (FIG. 3). The liberation of tyrosin was followed only in the TR 16 peptide that had been treated with TFA, whereas the effect of CPY on the two other samples led to separation of an amino acid that behaved in the same manner as synthetic tyrosin-O-sulfate. Thus, the tyrosin group in position 64 of the hirudin-PA as also identified as a tyrosin-O-sulfate group. However, the most surprising result was determination of Glu as a C-terminal amino acid. Since no attachment point for this group had been ootained during the automatic sequencing of the TR 16, it had to have been coupled to the carrier completely through C-terminal and side chain carboxyl groups, which meant that it was not accessible to an identification. Asp is only poorly hydrolysed by CPY and thus constitutes a limiting factor in the decomposition. It is thus rendered more difficult to coordinate the series of the C-terminal amino acids, since two Asp are present close to each other in the sequence, and Pro had not been detected. For this reason, the C-terminal sequence by CPY decomposition should only be indicated as -Tyr-Asp-Glu.

FIG. 3: Time diagram for the CPY catalyzed liberation of the amino acids of the C-terminus of hirudin-PA.

Hirudin-PA was incubated with CPY (40/1=w/w) in a 10 mM phosphate buffer pH 4.7 at 37° C. Aliquotic samples were taken from the incubation batch at specific times, adjusted to pH 2.0 and lyophilised. The lyophilisate was analyzed for liberated amino acids on the amino acid analyzer. No prolin was detected. The C-terminal sequence was determined as -Tyr-Asp-Glu.

The complete sequence for hirudin-PA is reproduced below and is shown in FIG. 4.

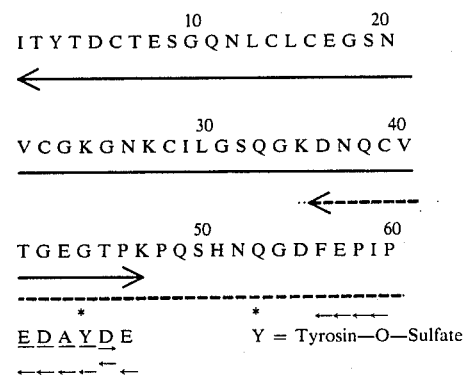

Sequence of the amino acid blocks in hiruding-PA, identified as follows:

←—→direct Edman decomposition of native and oxidized hirudin-PA
←——→Edman decomposition of trytic peptide
←—←—←—enzymatic decomposition by CPY The decomposition products of the hirudin-PA according to the present invention can be obtained by enzymatic decomposition of the hirudin-PA in the form of a limited proteolysis. To this end, one uses peptidases, such as carboxydiases, i.e., proteases, which split off an amino acid chain from the carboxyl end and/or amino peptidases, i.e., proteases that attack an amino acid chain from the amino end. Carboxypeptidases A, leucinaminopeptidase and the A,B,C, and D kathepsines are suitable proteases that can also be bound to the carrier; however, carboxypeptidase Y and kathepsin C are particularly well suited.

It is known that kathepsin C as a dipeptidylaminopeptidase splits off dipeptides sequentially from the unsubstituted amino end of the protein. However, it was found that kathepsin C also has C-terminal exopeptidase activity during the proteolysis of hirudin, so that the decomposition of hirudin-PA with kathepsin C can also be managed from the C-terminal end.

It is preferred that the proteolysis of hirudin-PA be done with kathepsin C. Incubation is best carried out at 37° C. The pH optimum of the enzymatic activity of kathepsin C lies in the weakly acidic area of DH 5 to 6.

The separation of the product mixture obtained after proteolysis is conducted with HPLC. As an example, one can use a Supelco column LC-18-DB or a Lichrospher column 100 CH-18/2. A gradient of 0.1% trifluoracetic acid in water (V/V; Buffer A) and 0.1% trifluoracetic acid in acetonitrile with 40% bufferA (V/V) has proved to be effective as an eluting agent.

According to the present invention the desulfohirudins-PA can be obtained if one liberates the phenolic hydroxy group of the tyrosin radical in position 64, present as sulfuric acid monoester in hirudin-PA of the formula given above.

Liberation of this group corresponding to the formula

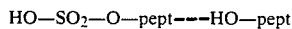

HO—SO$_2$—O—pept ---HO—pept (wherein pept stands for the residual portion of the hirudin) can be completed, for example, by hydrolysis, both chemical and biological methods being applicable for this purpose.

During chemical liberation it is preferred that the process be completed under the general conditions of acid catalysed hydrolysis, as under the action of a diluted aqueous hydrochloric acid solution, e.g., containing 2- to approximately 4N, preferably in trifluoracetic acid, as reaction medium, or with trifluoracetic acid that contains water, alone as reaction agent and solvent. In order to keep the danger of the hydrolitic separation of peptide compounds to a minimum, it is recommended that work be carried on under mild reaction conditions, e.g., at temperatures not in excess of room temperature, and the progress of the reaction be monitored analytically, i.e, by means of thin-film chromatography.

However, the hydrolysis is best completed by biological methods, in particular by the use of specific enzymes, arylsulfatases, which split off the phenolic sulfate ester groups to free phenolic groups under mild conditions. The biological liberation of the sulfated hydroxyl groups can be completed with the help of a suitable enzyme preparation with an enriched substance biocatalyst or an isolated enzyme, or one can use a suitable enzyme system in situ, as is immediately available, e.g., a growing or static microorganism, a cell culture, a cell homogenate, or an autolysate. One of the greatest advantages of biological hydrolysis is its high level of selectivity, that brings about only the desired separation of the monosulfate ester bonding, without attacking the remaining functional groups, mainly the peptide compounds in the sensitive starting material. In the main, the compounds according to the present invention are produced in that one treats hirudin-PA in an aqueous, preferably buffered, solution or suspension with an individual aryl sufatase preparation, e.g., of the arylsulfatase of Helix pomatia at a temperature that is usual for enzymatic processes, such as approximately 20°–45° C., preferably 25°–30° C. It is preferred that the work be done in a weakly acidic reaction, i.e., at a pH of approximately 4–7, in particular from approximately 5–6, which is adjusted with a buffer, such as an approximately 0.03 to approximately 0.3 molar solution of a salt of an organic carboxylic acid with an alkali metal or with an organic base, e.g., with sodium acetate or in particular pyridin acetate (of pH approximately 5.4). The ratio of enzyme used to the substrate (hirudin) is generally determined by the activity of the preparation in question, and normally amounts to approximately 1:2 to approximately 1:100, in particular from approximately 1:5 to approximately 1:20; it is preferable to use the purest possible enzyme preparations and those that are the most active. Since the arylsulfatases catalyse not only the separation but also the introduction of the sulfate group and bring about an adjustment of an equilibrium of the starting and the end substances, it is advantageous to establish the optimal concentration, quantity ratios to the substrate and times for desulfatisation for each enzyme preparation, by means of preliminary experimentation. As a rule, however, the reaction ends in a few minutes; the quality of the reaction products is not influenced even by longer contact (up to approximately 4 hours) with active enzyme (e.g., if the reaction mixture is left to stand).

The course of the enzymatic desulfatisation can be monitored bioanalytically on the samples that have been taken: practically, one proceeds, for example, in that the enzyme activity is destroyed by briefly (for approximately 3 minutes) heating the sample to approximately 100° C. and the substrate is treated with a carboxypeptidase Y. (The carboxypeptidase Y breaks down the peptide chain from the carboxy side, in that the amino acids are split off one after the other by splitting the respective amine bonds). Normally, the breakdown of the peptide chain is so advanced after some 15 minutes that the sulfatised and/or free amino acid in position 64 (Tyr64) is split off completely and thus accessible to determination in a conventional amino acid analyser.

The E,D-shortened desulfatohirudins result through splitting off of the two C-terminal amino acid building blocks Glu and Asp in the course of the hydrolysis of hirudin-PA. The separation of the mixture that results during this can be monitored preparative by HPLC chromatography. The desulfatohirudins-PA possess the same biological properties as hirudin-PA.

The compounds according to the present invention can be present in free form and as salts. Since they contain free amino groups or amidino groups, they can also be present in the form of acid additive salts. In particular, physiologically tolerable salts with normal, therapeutically usable acids are suitable as additive salts. The halogen hydracids, for example, hydrochloric acid, and even sulfuric acid and phosphoric or pyrophosphoric acid can be cited as inorganic acids. As organic acids, one can use sulfonic acids, for example, dibenzol or p-toluol-sulfonic acid or lower alkane sulfonic acids such as methane sulfonic acid, on the other hand carboxylic acid, such as acetic acid, lactic acid, palmitic acid, and stearic acid, malic acid, tartaric acid, ascorbic acid and/or oxalic acid. Since, on the other hand, the compounds according to the present invention also contain free carboxyl groups, they can be present as the salt of a base, e.g., as sodium, potassium, calcium or magnesium salt, or as ammonia salt or as salt of a physiologically tolerable organic base that contains nitrogen.

According to the procedure, the compounds according to the present invention can be extracted in free form or in the form of acid additive salts, inner salts, or salts with bases. The free compounds can be extracted from the acid additive salts in the known way. From the latter one can extract therapeutically useful acid additive salts by conversion with acids, e.g., with such acids as form the above named salts, evaporation or lyophilisation. The inner salts can be extracted by adjustment of the pH to a suitable neutral point.

The present invention also relates to pharmaceutical preparations that contain the compounds according to the present invention, or their therapeutically useful salts, optionally together with a pharmaceutical carrier and/or accessory agents.

These compounds can be used in particular in the presence of the above indications if, for example, they are used parenterally (intravenously, intracutaneously, intramuscularly, or subcutaneously), orally, or topically. In the first instance, the dosage used will depend on the specific form of use and the purpose of the therapy or prophylaxis. The size of the individual doses and the administration regimen can be best determined on the basis of an individual assessment of the particular case; the methods needed to determine relevant blood factors are familiar to the expert. In the normal case, the therapeutically effective quantity of the compounds according to the present invention, administered by injection, is in the dosage range of approximately 0.005 to approximately 0.1 mg/kg body weight. The range from approximately 0.01 to approximately 0.05 mg/kg body weight is preferred. Administration is by intravenous, intramuscular, or subcutaneous injection. Accordingly, pharmaceutical preparations for parenteral administration in single dose form contain approximately 0.4 to approximately 7.5 mg of the compound per dose, according to the invention, depending on the method of administration. In addition to the effective agent, these pharmaceutical preparations normally contain a buffer, e.g., a phosphate buffer that is intended to keep the pH between approximately 3.5 and 7, as well as sodium chloride, mannitol or sorbitol to adjust isotonicity. They can be present in freeze-dried or dissolved form, in which connection the solutions can advantageously contain an antibacterial conservation agent, for example, 0.2 to 0.3% 4-hydroxybenzoic acid methyl ester or -ethyl ester.

A preparation for topical use can be in the form of an aqueous solution, lotion or jelly, an oily solution or suspension, or a salve that contains grease or emulsion. A preparation in the form of an aqueous solution is obtained, for example, in that one dissolves the substance according to the present invention or a therapeutically useful salt therefrom in an aqueous buffer solution of pH 4 to 6.5 and, if desired, adds an anti-inflammatory agent and/or a polymer adhesive, for example polyvinylpyrrolidon, and/or a conserving agent. The concentration of the effective substance is approximately 0.08 to approximately 1.5 mg, preferably 0.25 to 1.0 mg in approximately 10 ml of a solution or 10 g of a jelly.

An oily applicational form for topical administration is obtained, for example, by suspending the substance according to the present invention or a therapeutically useful salt thereof in an oil, with the optional addition of a bulking agent such a aluminum stearate and/or surface reactants (tensides) of which the HLB (Hydrophilic-lipophilic-balance) factor is below 10, such as fatty acid monoesters of polyvalent alcohols, for example, glycerine monostearate, sorbitane monolaurate, sorbitane monostearate or sorbitane monooleate. A greasy salve is obtained, for example, by suspending the substances according to the present invention or the salts in a coatable grease base, optionally with the addition of a tenside having an HLB factor of less than 10. An emulsion salve is obtained by preparation on a powdered milk sugar base using an aqueous solution of the substance according to the present invention or the salts in a soft, coatable grease base with the addition of a tenside, the HLB factor of which is less than 10. All these forms for topical administration can contain preservatives. The concentration of the effective substance is approximately 0.08 to approximately 1.5 mg, preferably 0.25 to 1.0 mg in approximately 10 g of the basic mass.

In addition to the above describe pharmaceutical preparations and the analogs therof, which are suitable for direct-medical use on the human body or on the body of a mammal, the present invention applies to pharmaceutical preparations and compounds for medical use outside the living human or mammal body. Such compounds and preparations are used primarily as anticoagulants in blood that is subjected to circulation or treatment outside the body (e.g., dialysis in artificial kidneys), conservation or modification (haemoseparation). In their composition preparations of this kind, such as stock solutions or packaged in single-dose form, are similar to the above described injection preparations; however, more advantageously, the quantities or concentrations of the substances are related to the volume of blood that is to be treated or, more precisely, to the thrombin content of such blood. In this connection, it is to be noted that the substances according to the present invention (in free form)

(a) deactivate an approximate 5-fold quantity by weight of thrombin;

(b) are physiologically harmless even in larger quantities;

(c) are separated out of circulating blood even at high concentrations, so that there is no danger of overdose even in the case of transfusion, for example. According to the specific purpose, the suitable dose amounts to approximately 0.01 to 0.1 mg substance per liter of blood, and even then the upper limit can be greatly exceeded with no danger.

The bioanalytical use of the compounds according to the present invention and their salts used to analyze thrombin also form part of the objects of this invention, as well as preparations that contain the substances according to this invention, used for this purpose, e.g., mixtures of solids and above all solutions, in particular aqueous solutions; this can advantageously contain inert accessory substances in addition to the precise quantity or concentration of the substance according to the invention (also in the form of a salt), for example, those discussed above among the injection preparations which fulfill, for example, a stabilising and/or conserving role. These preparations are used to analyse thrombin in an analogous manner during bioanalysis.

Furthermore, the compounds according to the present invention can be used to preserve blood. To this end, blood preservatives are added to these compounds in a quantity of 0.1–2%-wt.

In the preceding description and in the claims, the abbreviated designations for amino acids and their radicals are used in keeping with the generally accepted rules of nomenclature and relate to alpha-amino acids and the radicals thereof, of the naturally occurring L-series.

EXAMPLE 1

2.5 g crude hirudin (extracted by fractionated precipitation with acetone) were dissolved in 20 ml elution buffer and put in a Sephadex G-75 medium column (3.8×150 cm). 0.05M triethanolamine, 0.4M NaCl, 0.02% NaN₃, pH 7.8 was used as an elution buffer. Throughput 55 ml/hr; fraction volume: 9.7 ml.

The fractions that were inhibitor active against thrombin were combined (300 to 400 ml), desalinated in an Amicon ultrafiltration cell with UM-05 membrane, and lyophilised.

The lyophilisate was subjected to anion exchange chromatography on DEAE cellulose (DE-52, Whatman; 2.5×100 cm).
Equilibrating buffer: 0.03 M ammonium acetate, pH 6.5.
Throughput: 25 ml/hr; fraction volumes: 8.3 ml.

After dissolution 1.4 g of the inhibitor was added to 10 ml of the equilibrating buffer.

The column was developed with equilibrating buffer until the chymotryptic inhibition activity had been eluated. The elutriation was carried out with a sodium acetate buffer of pH 6.0 composed as follows: 0.2M NaAc, 0.19M NaCl, 0.02% NaN₃.

The thrombin inhibiting fractions were combined, desalinated as described above by ultrafiltration, and lyophilised.

An equilibrating buffer of 0.2M sodium acetate, 0.19M NaCl, pH 6.0, was used for the subsequent chromatography on DEAE-Sephadex A-25 (column 1.9×68 cm). Throughput: 11 ml/hr; fractions volumes: 3.7 ml.

After dissolution and adjustment of the pH value, 6.3 mg of the inhibitor was added to 10 ml of the equilibrating buffer.

The column was developed for 2 hours with equilibrating buffer, then converted to the same buffer of pH 5.0, and equilibrated for a further 14 hours.

The column was elutriated with a linear pH gradient (the same buffer as above, pH 3.7).

The thrombin inhibiting fractions, which had been elutriated at approximately pH 4.6 to 4.7, were concentrated to approximately 3 ml.

Finally, lyophilisation was carried out, desalination completed on Sephadex G-25 with water as the washing agent, and lyophilisation completed once more.

The lyophilisate was broken down by means of RP-HPLC on Lichrospher 100 CH-18/2, 5μ, 4.6×250 mm. Elutriation was carried out with 0.1% trifluor acetic acid in water (V-V; Buffer A) and 0.1% trifluoracetic acid with acetonitrile with 40% buffer A (V-V; Buffer B). The elutriation took place isocratically with a solution of 63% buffer A and 37% buffer B (V-V). Flow: 1 ml/minute. Detection: at 214 and 254 nm.

The eluate obtained during a retention time of 9.6 minutes contains hirudin-PA, which was obtained after lyophilising in substance.

EXAMPLE 2

Production of the desulfated derivatives by incubation with arylsulfatase (ARS)

ARS-parent solution: 0.1 ml ARS suspension was diluted with 0.1M ammonium acetate, pH 5.5, to 2.5 ml and desalinated on a PD 10 column.
Hirudin-PA parent solution: 2 mg/ml buffer.
Buffer: 0.1M ammonium acetate, ph 5.5

Hirudin-PA parent solution and ARS parent solution were mixed in the proportion of 1:10 (V/V) and incubated at 25° C. The time sequence of the reaction was monitored by HPLC. After an incubation period of 24 hours it was heated to 90° C. for 3 minutes and the mixture broken down by HPLC under the following conditions:
Column: Lichrospher 10 CH-I8/2, 5μ, 4.6×250 mm.
Buffer A: 0.1% trifluoracetic acid in water (V/V)
Buffer B: 0.1% trifluoracetic acid in acetonitrile with 30% buffer A (V/V)
Flow: 1 ml/minute
Detection: at 214 nm
Temperature: 25° C.
Elution: isocratically with 66% buffer A and 34% buffer B (V/V)

EXAMPLE 3

Production of the reduction product of hirudin-PA

Hirudin-PA solution (2 mg/ml buffer) katepsin C parent solution (20 U/1, 14 ml) were mixed in the proportion of 1:5 (V/V) and incubated at 37° C. The course of the proteolysis was monitored by RP-HPLC. The split batch [Spaltansatz] is separated off preparitively by means of HPLC. The conditions were as cited in Example 2.

The embodiments of the invention in which an exclusive property or privilege is claimed are defined as follows:

1. A hirudin-PA compound of the formula I:

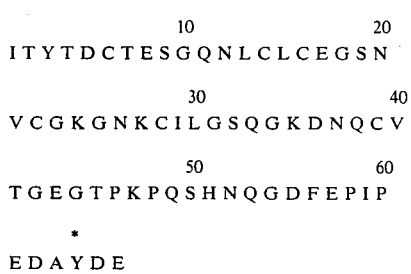

in which the above letters represent proteinogenic amino acids corresponding to the IUPAC nomenclature, said amino acids being peptidically bonded, and in which Y* is tyrosin, tyrosin-O-sulfate, or derivatives thereof, shortened by up to 2 amino acids at the N-terminus, and the amino acid chain at the C-terminus is shortened by the sequence

```
QSHNQGDFEPIPEDAY*DE,
       EPIPEDAY*DE,
         PIPEDAY*DE,
            EDAY*DE, or
               AY*DE,
``` or, if Y* is tyrosin, the amino acid chain is shortened by the sequence D E or E at the C-terminus, or a pharmaceutically useful salt thereof.

2. Hirudin-PA derivatives as in claim 1 of the general formula I, wherein the amino acid chain is abbreviated at the N-terminus by the sequence I or IT.

3. The hirudin-PA compound as in claim 1, wherein Y* is tyrosin-O-sulfate or a pharmaceutically useful salt thereof.

4. A desulfato hirudin-PA compound as in claim 1, wherein Y* is tyrosin or a pharmaceutically useful salt thereof.

5. A desulfato hirudin-PA compound as in claim 1 having the formula:

```
            10              20
    ITYTDCTESGQNLCLCEGSN
            30              40
    VCGKGNKCILGSQGKDNQCV
            50              60
    TGEGTPKPQSHNQCDFEPIP
            *
    EDAYD
``` wherein Y* is tyrosin is a pharmaceutically useful salt thereof.

6. A desulfato hirudin-PA compound as in claim 1 having the formula:

```
            10              20
    ITYTDCTESGQNLCLCEGSN
            30              40
    VCGKGNKCILGSQGKDNQCV
            50              60
    TGEGTPKPQSHNQGDFEPIP
            *
    EDAY
``` wherein Y* is tyrosin or a pharmaceutically useful salt thereof.

7. The hirudin-PA compound of claim 1, which comprises 66 amino acids having a molecular weight of 7087 and a specific antithrombin activity of 680–720 IU/mg.

8. A method for inhibiting blood clotting in humans or animals, which comprises administering a therapeutically effective amount of the hirudin-PA compound of claim 1 to a subject.

9. The method according to claim 8, which comprises administering about 0.005 to about 0.1 mg/kg by body weight of said compound to the subject by intravenous, intramuscular or subcutaneous injection.

10. A composition comprising an effective thrombin inhibiting amount of the hirudin-PA compound of claim 1 and a pharmaceutically acceptable carrier therefor.

11. A topical preparation comprising the composition of claim 10.

* * * * *